United States Patent [19]

Wimmer et al.

[11] Patent Number: 5,055,617

[45] Date of Patent: Oct. 8, 1991

[54] PROCESS FOR THE PREPARATION OF N-ALKYLATED ANILINES

[75] Inventors: Peter Wimmer; Hans-Josef Buysch, both of Krefeld; Lothar Puppe, Burscheid; Christian Froehlich, Krefeld, all of Fed. Rep. of Germany

[73] Assignee: Bayer Aktiengesellschaft, Leverkusen, Fed. Rep. of Germany

[21] Appl. No.: 552,277

[22] Filed: Jul. 12, 1990

[30] Foreign Application Priority Data

Jul. 28, 1989 [DE] Fed. Rep. of Germany ....... 3924999

[51] Int. Cl.$^5$ .................... C07C 209/18; C07C 253/30
[52] U.S. Cl. .................................... 564/401; 564/399; 558/418
[58] Field of Search ................. 564/399, 401; 558/418

[56] References Cited

U.S. PATENT DOCUMENTS

| | | | |
|---|---|---|---|
| 1,799,722 | 4/1931 | Arnold | 564/401 |
| 2,565,842 | 8/1951 | Hetzner et al. | 564/401 |
| 3,957,874 | 5/1976 | Dockner et al. | 564/401 |
| 4,029,707 | 1/1977 | Hargis | 564/401 |
| 4,400,537 | 8/1983 | Weil | 564/402 |
| 4,613,705 | 9/1986 | Hargis | 564/409 |
| 4,801,752 | 1/1989 | Chen et al. | 564/401 |

FOREIGN PATENT DOCUMENTS

| | | |
|---|---|---|
| 2335906 | 2/1975 | Fed. Rep. of Germany . |
| 577901 | 6/1946 | United Kingdom . |
| 915186 | 1/1963 | United Kingdom . |

OTHER PUBLICATIONS

Houben-Weyl, Methoden der organischen Chemie, vol. X1/1; Stickstoffverbindungen II; 1957, pp. 112-119; George Thieme Verlag; Stuttgard, DE.

Primary Examiner—Richard L. Raymond
Assistant Examiner—P. O'Sullivan
Attorney, Agent, or Firm—Sprung Horn Kramer & Woods

[57] ABSTRACT

Anilines or N-alkyl-anilines are advantageously reacted with alkyl alcohols or the associated dialkyl ethers at elevated temperature in the gas phase, if a $\gamma$-$Al_2O_3$ is used that is prepared by dehydration of an aluminum oxide/hydroxide hydrate and has a BET surface area from 50 to 400 $m^2/g$ and a surface acidity of 5 to 600 mmol $H^+$/kg.

13 Claims, No Drawings

PROCESS FOR THE PREPARATION OF N-ALKYLATED ANILINES

BACKGROUND OF THE INVENTION

1. Field of the Invention

The invention relates to a process for the preparation of N-alkylated anilines by reacting non-alkylated or only monoalkylated anilines with lower alcohols or the associated ethers at elevated temperature in the gas phase in the presence of an acid aluminum oxide catalyst.

Alkylated anilines are important industrial intermediates for the preparation of dyes, stabilizers, urethanes, ureas, pharmaceuticals and plant protection agents.

2. Description of the Related Art

It is known to prepare N-alkylated anilines by reacting anilines with alcohols either in the liquid phase or in the gas phase in the presence of acid catalysts. In the liquid phase process the reaction is carried out in the presence of liquid catalyst such as, for example, sulphuric acid, hydrochloric acid or phosphorus trichloride. These processes require a procedure under pressure. Because of the highly corrosive action of the acid catalysts the process must be carried out in special corrosion-resistant autoclaves. Nevertheless corrosion is not to be avoided. Additionally, the separation and disposal of the catalyst requires an additional expenditure.

In contrast, gas phase processes are carried out without pressure. Thus, according to the process described in DE-AS 10 31 796, a mixture of aniline vapour and alcohol vapour is passed through hot phosphoric acid at atmospheric pressure. In addition to corrosion problems, this process has the disadvantage that over a period of time the relatively large amount of phosphoric acid becomes unusable as catalyst and must be replaced by fresh phosphoric acid. The consumed catalyst must be sent for specialist disposal.

It is further known to carry out the alkylation of aromatic amines with alcohols on catalysts containing transition metals. U.S. Pat. No. 4,613,705 describes for example a vanadium/tin oxide contact catalyst. The conversion of aniline on this catalyst is however unsatisfactory and a high proportion of undesired ring alkylated products is found.

Houben-Weyl, Methoden der organischen Chemie (Methods of Organic Chemistry), volume XI/1 (1957), p. 116 discloses that aluminum oxides or silicates are also suitable catalysts for the alkylation of aromatic amines. However, as is further described, these catalysts have the disadvantage that their activity declines too rapidly and the life span is not sufficient for industrial purposes.

DE-AS 2,335,906 teaches that catalysts having a long service life are obtained if 0.1 to 20% by weight of phosphoric acid are added to silica. In order to avoid a rapid deactivation in this instance also and to ensure a long life span of the contact catalyst, it is necessary continuously to introduce phosphoric acid and/or alkyl phosphates during the alkylation; however, a portion of these phosphorus compounds is always discharged and must be separated from the reaction product.

Consequently the object was to make available catalysts with which different types of aniline compounds can be alkylated on the N atom in the gas phase and which do not possess the previously mentioned disadvantages. The catalysts must be distinguished by ready availability, long service lives and high activities and guarantee high conversion with good selectivity.

SUMMARY OF THE INVENTION

Surprisingly, it has now been found that certain aluminum oxides which are described in more detail further below, constitute more advantageous catalysts for the N-alkylation of anilines with alcohols than those known hitherto. The new process guarantees the high yields and conversions required, practically no ring alkylation occurs and the catalysts used have very long service lives.

Consequently the invention relates to a process for the N-alkylation of anilines or N-alkyl-anilines with lower alcohols or the associated dialkyl ethers at elevated temperature in the gas phase on $Al_2O_3$ catalysts, which is characterized in that the catalyst used is a $\gamma$-$Al_2O_3$ that is prepared by calcination of an aluminum oxide/hydroxide hydrate at 500° C. to 1000° C. and has a BET surface area of from 50 to 400 m²/g, preferentially 100 to 350, particularly preferentially 150 to 300 m²/g, and a surface acidity of 5 to 600 mmol $H^+$/kg, preferentially 10 to 400 mmol $H^+$/kg, particularly preferentially 20–300 mmol $H^+$/kg.

DETAILED DESCRIPTION OF THE INVENTION

Aluminum oxide/hydroxide hydrates for the preparation of the catalysts to be used in accordance with the invention can be prepared by hydrolysis of aluminum salts, aluminum alcoholates, aluminum phenolates or other suitable hydrolysable aluminum compounds. The hydrolysis can be carried out in a known manner by dilute acids or dilute alkalis, in many cases also by water alone. The carrying out of a hydrolysis of this type is, in principle, known to the person skilled in the art. It has emerged that hydrolysates of aluminum alcoholates are particularly suitable for the preparation of catalysts which can be used in accordance with the invention. Aluminum alcoholates of this type originate particularly preferentially from the oxidation of trialkyl-aluminum compounds, for example from the Alfol ® process (Ullmanns Enzyklopädie der technischen Chemie (Ullmanns Encyclopedia of Industrial Chemistry), 4th edition, volume 7, pp. 208 and 5th edition, Vol. A 10, pp. 283).

In this process for the preparation of alcohols by oxidation of aluminum-organic compounds and hydrolysis with water of the alkoxy compounds formed, an aluminum oxide/hydroxide hydrate of special quality is obtained, that contains only very small amounts of impurities.

Aluminum oxide/hydroxide hydrates are peptized with mineral acids and/or organic acids such as, for example, $HNO_3$, HBr, HCl, $CH_3COOH$ inter alia, for the preparation of granules, extrudates, beads or powders that can be dispersed with water. In the preparation of the shaped articles the acid/aluminum oxide/hydroxide mixture is thoroughly kneaded in a kneader for a few minutes before processing. The moist shaped articles are then dried at 110° C. and calcined for three hours at 500° C. to 1000° C., the $\gamma$ modification of the $Al_2O_3$ being formed.

The aluminum oxides formed in this process have BET surface areas of from 50 to 400 m²/g.

As a result of the peptization with the acid a surface acidity of the granules of from 5 to 600 mmol H+/kg is obtained depending on the amount of acid used.

A further embodiment for the preparation of the Al$_2$O$_3$ granules for the process according to the invention consists in using a pre-peptized, water-dispersable aluminum oxide/hydroxide as the starting material. This powder is adjusted with water to the granulating moisture level and is processed with suitable shaping equipment into beads, extrudates and granules. The calcination is also carried out at 500° C. to 1000° C. in the course of three hours.

The granules again have a BET surface area of from 50 to 400 m$^2$/g.

The surface acidity of these granules is in the stated range, preferably at 20 to 300 mmol H+/kg.

It was not foreseeable that such special γ-Al$_2$O$_3$ catalysts having the properties described, emerge so favourably, with respect to the service life and the effectiveness, that, in contrast to the Al$_2$O$_3$ catalysts known from the literature, they are suitable for an industrial use.

The surface acidity of the γ-Al$_2$O$_3$ obtained, and consequently its suitability for the process according to the invention, is most easily determined by direct titration of this γ-Al$_2$O$_3$ in aqueous suspension.

The process according to the invention for the N-alkylation of anilines or N-monoalkyl-substituted anilines is carried out in the gas phase at 200° to 400° C., preferentially at 250° to 350° C., paarticularly preferentially at 260° to 320° C. In this process the catalyst can be arranged either in on fixed bed or in a fluidized bed. The process according to the invention is carried out at atmospheric pressure; it can however also be carried out at slightly reduced or slightly increased pressure. Consequently, a pressure range of 0.7 to 2 bars may be mentioned as the pressure range.

For example, to carry out the reaction a mixture of the aniline to be alkylated on the N-atom and the alkylating agent alcohol or ether can be vaporized and the vaporized mixture passed over the contact catalyst. It is possible to add to the feed mixture an inert gas, such as nitrogen, helium, water vapour, hydrogen or argon, as carrier gas.

The catalyst loading (Liquid Hourly Space Velocity=LHSV) can be varied in the range from 0.1 to 4.0 l/l h, preferably from 0.3 to 2.0 l/l h. In this context the LHSV is defined as the ratio of the volume of the aniline/alcohol or aniline/dialkyl ether mixture per catalyst volume per hour.

If the fixed bed process is used the catalyst is appropriately used in the form of granules; if the fluidized bed process is used a fine particle distribution is known to be suitable.

The reaction mixture is condensed at the reactor outlet and separated, for example by distillation. Unreacted starting materials can be fed back into the reaction in a known manner. For the case that N-monoalkylated or N,N-dialkylated anilines are to be prepared from anilines not substituted on the N atom, the anilines monosubstituted and disubstituted on the N atom are also separated as reaction products, the non-desired reaction product also being fed back into the reaction.

In the process according to the invention, anilines or N-alkyl anilines of the formula

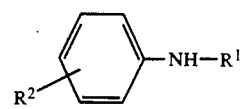

are used, in which,

R$^1$ denotes hydrogen or straight-chain or branched C$_1$–C$_{10}$-alkyl and

R$^2$ denotes hydrogen, straight-chain or branched C$_1$–C$_{10}$-alkyl, C$_6$–C$_{12}$-aryl, C$_1$–C$_4$-alkoxy, halogen, cyano or nitro.

Straight-chain or branched C$_1$–C$_{10}$-alkyl is, for example, methyl, ethyl, propyl, isopropyl, butyl, isobutyl, tert.-butyl, the isomeric hexyls, octyls or decyls. The said C$_1$–C$_4$-alkyl radicals may be preferentially named.

C$_6$–C$_{12}$-aryl is, for example, phenyl, naphthyl or biphenylyl, preferably phenyl, C$_1$–C$_4$-alkoxy is, for example, methoxy, ethoxy, propoxy, isopropoxy, butoxy or isobutoxy, preferably methoxy or ethoxy. Halogen is, for example, fluorine, chlorine or bromine, preferably chlorine.

The following may be listed, for example, as suitable amines: aniline, o-, m- and p-toluidine, o-, m- and p-chloro-aniline, 2,4-, 2,6-, 3,4- and 3,5-xylidine, o-, m- and p-ethylaniline, o-, m- and p-isopropylaniline and others; in particular aniline and the said toluidines may be singled out.

The lower alcohols familiar to the person skilled in the art, for example those having 1 to 4 C atoms, such as methanol, ethanol, propanol, isopropanol or the various butanols, may be mentioned as alcohols suitable for the alkylation.

Methanol or ethanol are preferably used. The associated dialkyl ethers (C$_1$–C$_4$-alkyl)$_2$O are also known to the person skilled in the art; these are dimethyl ether, diethyl ether, dipropyl ether, diisopropyl ether, dibutyl ether and the conceivable mixed ethers. Dimethyl ether or diethyl ether is preferentially used. If an ether is used, this is counted as two moles of the corresponding alcohol.

Depending on whether the radical R$^1$ in the formula (I) denotes hydrogen or an alkyl radical, the process according to the invention proceeds according to one of the two following equations:

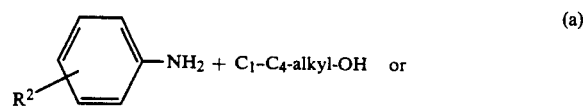

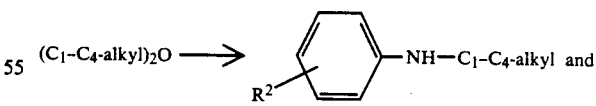

or

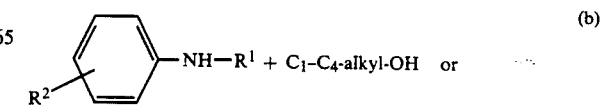

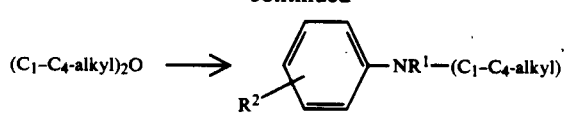

In the reaction according to a) an aniline not substituted on the N atom is converted by an alcohol or a dialkyl ether into a mixture of the aniline monosubstituted on the N-atom and the aniline disubstituted on the N atom. According to reaction b) an aniline already monoalkyl-substituted on the N atom is converted to an aniline dialkylated on the N atom. In this case, depending on the substituent $R^1$ already present, a mixed alkylated aniline can also be obtained.

The molar ratio of the alkylating agent alcohol or ether to aniline is 0.2 to 10 moles of alcohol or 0.1 to 5 moles of ether per mole of aniline or N-alkyl-aniline, preferentially 0.4 to 6, or 0.2 to 3, particularly preferentially 0.5 to 4, or 0.25 to 2. The choice of the molar ratio allows, in a manner known in principle to the person skilled in the art, the ratio of N-monoalkyl-aniline to N,N-dialkyl-aniline in the product to be controlled, if an aniline that is not yet substituted on the N-atom is used as starting material. An excess of alcohol relative to aniline brings about a shift in the selectivity in favour of the N,N-dialkyl-aniline. A low ratio of aniline to alcohol facilitates a high selectivity for N-monoalkylaniline.

If there is a large requirement for monoalkyl compounds, then any excess of dialkylaniline produced can be fed back into the reaction and converted into monoalkylaniline. The same also applies for the case that a large proportion of N,N-dialkyl compounds are required, then the monoalkylanilines can be recycled and alkylated to a higher degree.

EXAMPLES

Catalyst Preparation Example A 12 kg of 1.5% by weight $HNO_3$ were added in a constant stream over a period of 7 min. to 20 kg of aluminum oxide/hydroxide hydrate (for example Pural SCF ®, Condea company) in a kneader. A further 7 kg of 1.5% by weight $HNO_3$ were then added, with further kneading, over a period of 8 min. After shaping using appropriate granulating equipment the granules were dried at 110° C. and calcined for 3 hours at 550° C. The granules thus obtained had a surface acidity of 30 mmol $H^+$/kg.

Catalyst Preparation Example B 10 kg of a pre-peptized aluminum oxide/hydroxide hydrate (for example Dispersal spezial 10/1 ®, Condea company) were made granulation-moist with water and kneaded for about 15 min. in a kneader. The moist mixture was then processed into shaped articles, dried and calcined for three hours at 550° C. The granules thus obtained had a surface acidity of 90 mmol $H^+$/kg.

Catalyst Preparation Example C (Comparison)

500 g of commercially available $\gamma$-$Al_2O_3$ granules (Alumine Activee A, Rhone-Poulenc Co.) were impregnated with 0.5 ml of a 1N $HNO_3$ solution, dried and activated at 550° C. The material had a surface acidity of <5 mmol $H^+$/kg.

Determination of Acidity

To determine the surface acidity, 1 g of aluminum oxide granules ground to powder was suspended in 40 ml of water. The suspension was potentiometrically titrated with 0.1N NaOH, at a drip rate of 0.1 ml/min.

The grinding up of the samples of granules was carried out in a micro-dismembrator (Braun Melsungen AG). 5 ml of the granules and a tungsten carbide ball with a diameter of 9 mm were introduced into the lower part of a grinding mill. The mill was closed with the upper part and placed in the PTFE shaking-container. The shaking-container was fastened in the holder of the dismembrator and the vibration amplitude set to a stroke of about 10 mm. The grinding was completed after 6 to 8 min. The fine powder could then be used for the above determination of acidity.

Examples 1–4

25 ml of the aluminum oxide according to Example A or B, that had an average particle size of from 1 to 2 mm and is to be used according to the invention were introduced into a vertical reaction tube 40 cm in length and with a diameter of 30 mm. Thermostat control of the reactor was possible by means of an organic heat transfer medium. The temperature in the catalyst bed could be measured using a movable thermocouple and was 300° C. A mixture of aniline and alcohol in the molar ratio 1:1 was metered into a vaporizer via a metering device, converted in the vaporizer into the gas phase and passed over the contact. The metering speed was 20 ml/h of liquid mixture; this corresponded to a catalyst loading (LHSV) of 0.8 1/1/h. The reaction product was condensed out and analyzed by gas chromatography.

Conversion and selectivity are compiled in Table 1.

Comparative Examples 1 and 3

A commercially $\gamma$-aluminum oxide, that had not been prepared by the hydrolysis of aluminum alcoholates or aluminum salts, but originated, for example, from the Bayer processes (Ullmann, 4th edition, vol. 7, pp. 305 and 5th edition Vol. A 1, pp. 566) and has a low surface acidity, was used as catalyst in the equipment from Example 1 to 4, under identical conditions. The comparative experiments are also given in Table 1.

Comparative Examples 2 and 4

The catalyst obtained in accordance with preparation example C was used in the equipment from example 1 to 4 under identical conditions. The results are also recorded in Table 1.

According to Examples 1 to 4 the $\gamma$-aluminum oxides to be used according to the invention are good catalysts for the N-alkylation of anilines with alcohols in the gas phase at atmospheric pressure. From Table 1 it is clearly apparent that the $\gamma$-aluminum oxides which were not prepared according to the invention are indeed also catalytically active but exhibit an unsatisfactory degree of conversion although they have a larger BET surface area than the aluminum oxides to be used in accordance with the invention. In spite of the lower degree of conversion, the proportion of undesired ring alkylation products was larger than with the aluminum oxides to be used in accordance with the invention. A slight increase of the activity of the aluminum oxide materials not prepared in accordance with the invention can be effected by a subsequent treatment with acid. However the degree of conversion still remains clearly below the level achievable with the catalysts to be used in accordance with the invention. The subsequent treatment with acid has no effect whatever upon the methylation of aniline.

TABLE 1

N-alkylation of aniline with alcohols

| | | Catalyst | | | | Selectivity (%) | | |
|---|---|---|---|---|---|---|---|---|
| Example | Cat. | acidity (mmol $H^+$/kg) | BET surface area ($m^2$/g) | Alcohol | Aniline conversion (%) | N-alkyl-aniline | N,N-di-alkyl-aniline | Ring alkyl |
| 1 | A | 30 | 230 | EtOH | 69 | 89.4 | 9.7 | 0.9 |
| 2 | B | 90 | 160 | EtOH | 66 | 89.8 | 9.4 | 0.8 |
| Comparative 1 | (1) | <5 | 280 | EtOH | 49 | 92.2 | 6.4 | 1.4 |
| Comparative 2 | C | <5 | 280 | EtOH | 58 | 91.0 | 7.7 | 1.3 |
| 3 | A | 30 | 230 | MeOH | 72 | 67.7 | 32.0 | 0.3 |
| 4 | B | 90 | 160 | MeOH | 74 | 61.5 | 38.1 | 0.4 |
| Comparative 3 | (1) | <5 | 280 | MeOH | 63 | 70.6 | 28.8 | 0.6 |
| Comparative 4 | C | <5 | 280 | MeOH | 62 | 69.4 | 28.5 | 2.1 |

(1) commerically available γ-aluminum oxide granules Alumine Activee A from Rhone-Poulenc Co.

The following examples are intended to illustrate the flexibility of the process in respect of substrate variability and selectivity as well as the service life characteristics of the catalysts.

Examples 5 to 8

1 l of a γ-aluminum oxide according to Example A or B, that had an average particle size of 2 to 3 mm, was introduced into a vertical reaction tube 150 cm in length and with an internal diameter of 32 mm. Thermostat control of the reactor was possible using an organic heat transfer medium. The temperature above the total catalyst bed could be measured using a movable thermocouple. The liquid reaction mixture was fed into the vaporizer via a pump, converted into the gas phase and passed over the contact catalyst. The reaction product was condensed and analyzed by gas chromatography. The precise test conditions and the results of the examples 5 to 8 are summarized in Table 2.

The degree of conversion and selectivity were unchanged after 4000 hours catalyst loading.

The examples show that a very flexible control of the product selectivity is possible. The parameters which are responsible for the degree of alkylation are the catalyst loading (LHSV), the molar ratio of aniline to alcohol and the reaction temperature. A low ratio of aniline to alcohol at a high catalyst loading facilitates a very selective monoalkylation. At degrees of conversion of 45% and 49% respectively selectivities of 87% to 95% of monoalkylaniline are achieved (Examples 6, 8). Under analogous reaction conditions significantly lower degrees of conversion are achieved using aluminum oxides other than those to be used according to the invention. An excess of alcohol, a low catalyst loading and a high temperature lead to a high aniline conversion and high dialkyl selectivity, which can reach more than 90% (Example 7).

Example 9

A mixture of aniline and diethyl ether in the molar ratio 1:0.5 was reacted in accordance with Example 2, at 300° C. and a flow speed of 0.8 l/l/h. The degree of conversion of aniline was 69%. The selectivities were 87.2% for N-ethylaniline, 11.8% for N,N-diethylaniline and 1.0% for the sum of the ring-alkylated by-products.

TABLE 2

N-Alkylation of aromatic amines

| | | Catalyst | | | Aniline: | | | Aniline | Selectivity (%) | | |
|---|---|---|---|---|---|---|---|---|---|---|---|
| Ex. | Cat. | Acidity (mmol $H^+$/kg) | BET surface area ($m^2$/g) | Aniline Alk. agent | Alk. agent | LHSV (l/l/h) | T (°C.) | conversion (%) | N-mono | N,N-Di | Ring alkyl |
| 5 | A | 30 | 230 | aniline MeOH | 1:1 | 0.5 | 310 | 75 | 63.8 | 35.9 | 0.3 |
| 6 | B | 90 | 160 | aniline MeOH | 1:1 | 1.5 | 270 | 45 | 86.8 | 13.1 | 0.1 |
| 7 | B | 90 | 160 | aniline MeOH | 1:3 | 0.3 | 310 | 99 | 8.5 | 91.4 | 0.1 |
| 8 | B | 90 | 160 | m-tolu-idine EtOH | 1:1 | 1.5 | 300 | 49 | 94.8 | 4.5 | 0.7 |

What is claimed is:

1. A process for the N-alkylation of anilines or N-alkyl-anilines with lower alcohols or the associated dialkyl ethers at an elevated temperature of from about 200° C. to about 400° C. and at a pressure of 0.7 to 2 bars, in the gas phase on $Al_2O_3$ catalysts, wherein the catalyst used is a γ-$Al_2O_3$ that is prepared by dehydration of an aluminum oxide/hydroxide hydrate and has a BET surface area of from 50 to 400 $m^2$/g and a surface acidity of 5 to 600 mmol $H^+$/kg wherein a $C_1$–$C_4$-alcohol or the associated di-$C_1$–$C_4$-alkyl ether is used in an amount of from 0.2 to 10 moles of alcohol or 0.1 to 5 moles of ether per mole of aniline or N-alkyl-aniline, which process is carried out at a catalyst loading (Liquid Hourly Space Velocity=LHSV) of 0.1 to 4.0 l/l/h, understood as the volume of the aniline/alcohol or aniline/ether mixture per catalyst volume per hour.

2. The process of claim 1, wherin the γ-$Al_2O_3$ is prepared by dehydration of a hydrolysate of aluminum alcoholates.

3. The process of claim 2, wherein an aluminum alcoholate from the oxidation of trialkylaluminum compounds is used.

4. The process of claim 1, wherein the γ-$Al_2O_3$ has a BET surface area from 100 to 350 $m^2$/g.

5. The process of claim 4, wherein the γ-$Al_2O_3$ has a BET surface area of from 150 to 300 $m^2$/g.

6. The process of claim 1, wherein the γ-$Al_2O_3$ has a surface acidity of 10 to 400 mmol $H^+$/kg.

7. The process of claim 6, wherein the γ-$Al_2O_3$ has a surface acidity of 20 to 300 mmol $H^+$/kg.

8. The process of claim 1, which is carried out at 250° to 350° C.

9. The process of claim 8, which is carried out at 260° to 320° C.

10. The process of claim 1, wherein an aniline or N-alkyl-aniline of the formula

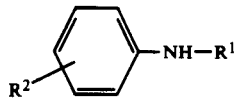

is used, in which $R^1$ denotes hydrogen or straight-chain or branched $C_1$–$C_{10}$-alkyl and $R^2$ denotes hydrogen, straight-chain or branched $C_1$–$C_{10}$-alkyl, $C_6$–$C_{12}$-aryl, $C_1$–$C_4$-alkoxy, halogen, cyano or nitro.

11. The process of claim 1, which is carried out at a catalyst loading of 0.3 to 2.0 l/l/h.

12. The process of claim 1, wherein the molar ratio is 0.4 to 6 moles of alcohol or 0.2 to 3 moles of ether per mole of aniline or N-alkyl-aniline.

13. The process of claim 12, wherein the molar ratio is 0.5 to 4 moles of alcohol or 0.25 to 2 moles of ether per mole of aniline or N-alkyl-aniline.

* * * * *